United States Patent [19]

Salituro et al.

[11] Patent Number: 5,051,442

[45] Date of Patent: Sep. 24, 1991

[54] 3-INDOLYL THIOACETATE DERIVATIVES AND NMDA RECEPTOR ANTAGONISTIC USE THEREOF

[75] Inventors: Francesco G. Salituro, Fairfield; Bruce M. Baron, Cincinnati, both of Ohio

[73] Assignee: Merrell Dow Pharmaceuticals Inc., Cincinnati, Ohio

[21] Appl. No.: 514,074

[22] Filed: Apr. 25, 1990

[51] Int. Cl.$^5$ .................. C07D 209/18; A61K 31/405
[52] U.S. Cl. ..................................... 514/419; 548/494
[58] Field of Search .................. 548/494; 514/419

[56] References Cited

PUBLICATIONS

Greenamyre, J. T., "Arch, Neurol.", vol. 43, pp. 1058–1063 (1986).
Olney, J. W., "Biol. Psychiatry", 26, pp. 505–525 (1989).
Robinson et al "Glutamate and Related Neurotransmitters", pp. 446–455.
Dingledine et al, TiPS, Aug. 1990 pp. 334–338.

*Primary Examiner*—David B. Springer
*Attorney, Agent, or Firm*—J. Michael Dixon

[57] ABSTRACT

The present invention is directed to a new class of 3-indolyl thioacetate derivatives which the NMDA antagonists.

25 Claims, No Drawings

3-INDOLYL THIOACETATE DERIVATIVES AND NMDA RECEPTOR ANTAGONISTIC USE THEREOF

The present invention is directed to a new class of 3-indolyl thioacetate derivatives which are useful as NMDA antagonists. Another aspect of this invention is directed to the use of these compounds in the treatment of a number of disease states such as, for example, epilepsy, stroke, etc. A further aspect of this invention is directed to pharmaceutical compositions containing these compounds.

In accordance with the present invention, a new class of NMDA antagonists have been discovered which can be described by the following formula:

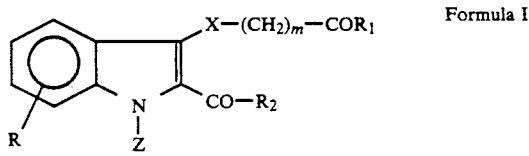

Formula I in which X is represented by S, SO, or $SO_2$; m is an integer from 1–4; Z is represented by H, $C_{1-4}$ alkyl, phenyl, substituted phenyl, or an alkylphenyl substituent in which the phenyl ring may be optionally substituted; R is represented by hydrogen, halogen, $C_{1-4}$ alkyl, $C_{1-4}$ alkoxy, $CF_3$, $OCF_3$, OH, $NO_2$, or CN; $R_1$ and $R_2$ are each independently represented by —OH, —$OR_3$, —$NR_4R_5$, —$OCH_2OR_3$, or —O—$(CH_2)_n$—$NR_6R_7$, in which n is an integer from 1–4; $R_3$ is represented by $C_{1-4}$ alkyl, phenyl, substituted phenyl or an alkylphenyl substituent in which the phenyl ring may be optionally substituted; $R_4$ and $R_5$ are each independently represented by hydrogen or a $C_{1-4}$ alkyl; $R_6$ and $R_7$ are each independently represented by hydrogen or a $C_{1-4}$ alkyl, or $R_6$ and $R_7$ together with the adjacent nitrogen atom form a piperidino, morpholino, or pyrrolidino group; and the pharmaceutically acceptable addition salts thereof.

As used in this application:
a) the term "halogen" refers to a fluorine, chlorine, or bromine atom;
b) the terms "lower alkyl group and $C_{1-4}$ alkyl" refer to a branched or straight chained alkyl group containing from carbon atoms, such as methyl, ethyl, n-propyl, isopropyl, n-butyl, isobutyl, etc.;
c) the terms "lower alkoxy group and $C_{1-4}$ alkoxy" refer to a straight or branched alkoxy group containing from 1–4 carbon atoms, such as methoxy, ethoxy, n-propoxy, isopropoxy, n-butoxy, isobutoxy, etc.;
d) the term "substituted phenyl ring" refers to a phenyl moiety ($C_6H_5$) which is substituted with up to 3 substituents, each substituent is independently selected from the group consisting of halogens, $C_{1-4}$ alkyl, $C_{1-4}$ alkoxy, $CF_3$, $OCF_3$, OH, CN, and $NO_2$. These substituents may be the same or different and may be located at any of the ortho, meta, or para positions.
e) the term "alkylphenyl substituent" refers to the following structure, —$(CH_2)_p$—$C_6H_5$, in which p is an integer from 1–3. This phenyl ring may be substituted in the manner described immediately above.
f) the expression pharmaceutically acceptable additions salts thereof refers to either acid addition salts or to basic additions salts;
g) the term sulfone refers to: SO, and;
h) the term sulfoxide refers to: $SO_2$.

The expression "pharmaceutically acceptable basic addition salts" is intended to apply to any non-toxic organic or inorganic basic addition salts of the compounds represented by Formula I or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono-or di-basic salts can be formed with those compounds.

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form.

The indole ring depicted in Formula I is always substituted at positions 2 and 3, and may be optionally substituted at position 1. It may be further substituted as is indicated by the possible definitions for R. R may represent up to 3 additional substituents and these additional substituents may be located at any of positions 4, 5, 6, or 7. These substituents can be the same or different.

$R_1$ and $R_2$ may contain either a phenyl or an alkylphenyl substituent in which the phenyl ring may be optionally substituted. There may be up to 3 substituents occuring on these phenyl rings and these substituents may be located at any of the ortho, meta, or para positions. The specific substitutions may be any of those listed above in the definition of substituted phenyl ring. Z may also be represented either by a substituted phenyl ring or an alkyl phenyl substituent in which the phenyl ring may be substitued. These phenyl rings may also contain up to 3 substitutents which may be located at any of the ortho, meta, or para positions. The specific substitutions may be any of those listed above in the definition of substituted phenyl ring.

$R_1$ and $R_2$ may be represented by the same substituent or differing substitutents. Likewise $R_4$ and $R_5$ may be represented by the same substitutent or differing substitutents. When $R_6$ and $R_7$ are represented by hydrogen or a $C_{1-4}$ alkyl, they may represent the same or differing substituents. When $R_6$ and $R_7$ form a hetrocyclic ring along with the indicated nitrogen atom, the nitrogen atom of the hetrocycle is always bonded to the adjacent alkylene group.

It is preferred that positions 4 and 6 of the indolyl ring be substituted. It is also preferred that these substituents be halogen atoms such as chlorine atoms.

Examples of compounds encompassed by the present invention include:

3-[(carbethoxymethyl)thio]-2-carbethoxy-4,6-dichloroindole,
3-[(carboxymethyl)thio]-2-carboxy-4,6-dichloroindole,
3-[(carbethoxymethyl)thio]-2-carbethoxyindole,
3-[(carboxymethyl)thio]-2-carboxyindole,
3-[(carboxymethyl)sulfinyl]-2-carboxyindole,
3-[(carboxymethyl)sulfonyl]-2-carboxyindole,
3-[(2-(2-dimethylamino)ethoxycarbonylmethyl)thio]-2-(2-dimethylamino)ethoxycarbonyl-4,6-dichloroindole,
3-[(carboxamidomethyl)thio]-2-carboxamidoindole,
3-[(carboxymethyl)thio]-2-carboxy-6-fluoroindole, and
3-[(carboxymethyl)thio]-2-carboxy-4,6-difluoroindole.

The compounds of Formula I in which X is represented by S can be prepared using techniques which are analogously known in the art. One method for preparing these compounds is disclosed below in Reaction Scheme I:

REACTION SCHEME I

STEP A

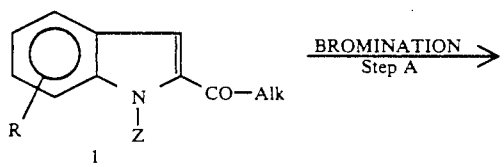

STEP B

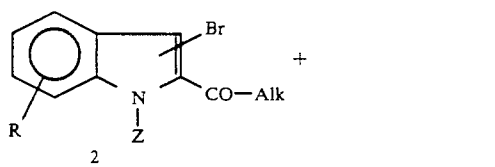

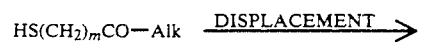

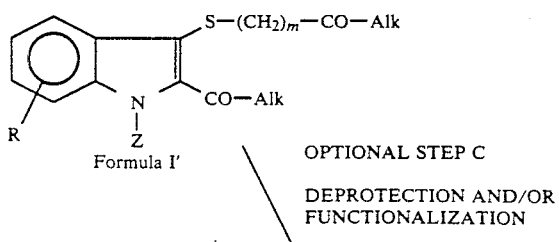

OPTIONAL STEP C

DEPROTECTION AND/OR FUNCTIONALIZATION

-continued
REACTION SCHEME I

FORMULA I

In Step A of Reaction Scheme I, the proper starting material is an indole derivative as described by structure (1) in which R and Z are as in Formula I, and Alk is a suitable protecting group, such as a linear $C_{1-4}$ alkoxy. Alternatively, any of the substituents represented by $R_2$, with the exception of OH, may also be present at this position. This compound is subjected to a bromination reaction in Step A which serves to introduce a bromine substituent at the 3-position of the indole ring. In Step B, the 3-bromo-indole as described by structure (2), is subjected to a displacement reaction with the alkyl thioacetate as described by structure (3) in which m is an integer from 1-4 and Alk is a suitable protecting group such as a linear $C_{1-4}$ alkoxy or is any of the substituents represented by $R_1$, other than OH. This displacement reaction produces the protected 3-indolyl thioacetate Of Formula I'.

Depending upon the substituents which $R_1$ and $R_2$ are to be represented by in the final product, it may be necessary to carry out a deprotection reaction as depicted in Step C and/or a functionalization reaction such as a transesterification, amidation, etc. These reactions can be carried out using techniques well known in the art. Alternatively, rather than carrying out a separate functionalization reaction, it is also possible to utilize an indole derivative of structure (1) or an alkyl thioacetate derivative of structure (3) in which $R_1$ and $R_2$ are represented by the same substituent as is desired in the final product. This is appropriate for any of the compounds except those in which $R_1$ or $R_2$ is to be represented by OH. This is especially appropriate for those compounds in which $R_1$ and $R_2$ are to be represented by differing substituents.

The bromination reaction of Step A can be carried out using techniques known in the art. The proper starting material is an indole derivative in which R and Z are represented by the same substituent as is desired in the final product of Formula I. The particular $C_{1-4}$ alkoxy which is utilized as a protecting group is not critical since it is not necessarily retained in the final product. Methods for producing these indole derivatives are known in the art. For example see, Brennan et al. *Heterocycles* Vol. 24, page 2879 (1986).

The bromination reaction can be carried out in the following manner. The indole derivative of structure (1) is contacted with an equivalent amount of pyridinium perbromide in an organic solvent such as pyridine. The reaction is typically carried out at a temperature range of from about 0° C. to about 25° C. for a period of time ranging from about 0.5 to about 1 hour. The 3-bromoindole derivative of structure (2) can be recovered from the reaction mixture by methods known in the art such as flash chromatography. It can then be optionally purifed by recrystallization from a solvent system such as ethyl acetate/hexane.

The displacement reaction of Step B can also be carried out using techniques known in the art. The 3- bromo-indole derivative produced above in Step A, is contacted with a molar excess of an alkyl thioacetate as described by structure (3) in which m is as in the desired product, and a base such as $K_2CO_3$. The reactants are typically contacted in an organic solvent such as acetone. The reactants are typically stirred together for a period of time ranging from about 4 hours to about 24 hours at a temperature range of from about room temperature to reflux. The resulting protected 3-indolyl thioacetate of Formula I' can be recovered from the reaction by techniques such as flash chromatography. It can then be optionally purified by recrystallization from a solvent system such as ethyl acetate/hexane.

Depending upon the substituent which is desired at the $R_1$ and $R_2$ positions, it may be necessary to subject the 3-indolyl thioacetate of Formula I' to a deprotection reaction and/or functionalization reaction. The deprotection reaction of Step C can be carried out using hydrolytic techniques known per se. Typically, the protected 3-indolyl thioacetate of Formula I' is subjected to a basic hydrolysis. The compound is contacted with a 2 to 3 molar excess of an inorganic base such as lithium hydroxide. The hydrolysis is carried out at a temperature range of from about 25° C. to about 50° C. for a period of time ranging from 1 to 5 hours. The desired compound of Formula I can then be recovered from the reaction zone by flash column chromatography and optionally purifed by recrystallization from a solvent system such as ethyl acetate/hexane.

The various ester and amide derivatives encompased by Formula I can be prepared by techniques known in the art. One method of preparing the ester derivatives is to contact a compound of Formula 1 in which $R_1$ and $R_2$ are represented by OH, with an alcohol corresponding to the desired ester in the presence of an acid such as sulfuric acid. The esterification is typically conduct at elevated temperatures. The desired compound of Formula I can then be recovered from the reaction zone by flash column chromatography and optionally purifed by recrystallization from a solvent system such as ethyl acetate/hexane.

Another suitable esterification method is to contact a compound of Formula I in which $R_1$ and $R_2$ are represented by OH with a base such as diethylisopropylamine, in a polar inert solvent such as dimethylformamide, dimethylsulfoxide, acetonitrile, acetone or tetrahydrofuran, thereby forming a bis carboxylate salt. The bis carboxylate salt is then contacted with 2 to 5 equivalents, preferably about 2.5 equivalents, of an alkylhalide corresponding to the desired ester, and allowed to react at a temperature of about 25° C. for a period of time ranging from 16-24 hours. The reaction mixture is then quenched with dilute aqueous acid and extractive work-up as is known in the art affords the diester compounds of Formula I, which can be purified by standard methods such as chromatography or recrystallization.

Amides can also be easily added to the compounds of Formula I by taking a compound of Formula I in which $R_1$ and $R_2$ are each represented by ester functions and contacting it with an excess of ammonia or a mono- or dialkylamine at a temperature of from 0-100° C. for a period of time ranging from 1-48 hours in an inert solvent such as tetrahydrofuran. The resulting amide derivatives of Formula I can then be isolated and purified by techniques known in the art.

Another method for producing amides or esters comprises contacting a compound of Formula I in which $R_1$ and $R_2$ are contacting a compound represented by —OH with a halogenating agent such as thionyl chloride, oxalyl chloride, phosphorus oxychloride, phosphorus pentachloride, etc. The resulting diacid halides are then contacted with an excess of ammonia, monoalkylamines, dialkylamines, aliphatic alcohols, aromatic alcohols or a dialkylamino alkyl alcohol such as dimethylaminoethanol, diethylaminoethanol, optionally in the presence of a base such as a tertiary alkylamine, in an inert solvent such as ether, dioxane, tetrahydrofuran, etc. at a temperature of from 0–25° C. for a period of time ranging from 5–16 hours. The resulting amides or esters can be isolated and purified by methods known in the art.

Those compounds of Formula I in which X is represented by SO or $SO_2$ can also be prepared using techniques that are analagously known in the art. One method for preparing these compounds is disclosed below in Reaction Scheme II:

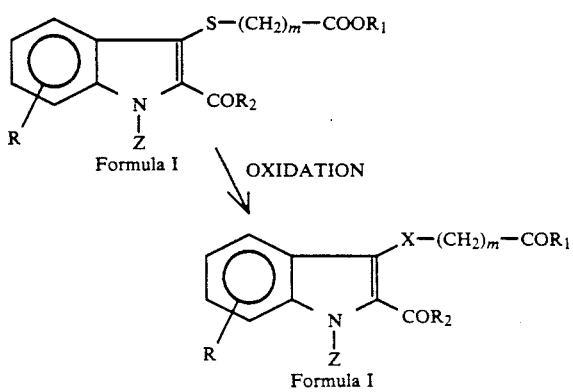

The first step is to prepare a compound of Formula I in which R, Z, $R_1$ and $R_2$ are represented by the same substituents as is desired in the final product and X is represented by S as is depicted. This can be done by the method depicted in Reaction Scheme I. If either $R_1$ or $R_2$ are to be represented by —OH in the final product, then these should be represented by a protecting group such as a $C_{1-4}$ alkoxy during the oxidation reaction. The compound is then subjected to an oxidation reaction which converts the sulfur substituent into a sulfone or sulfoxide substituent depending upon the manner in which the oxidation is carried out. Any protecting group can then be removed by hydrolytic techniques known per se.

If X is to be represented by a sulfone substituent, then the oxidation is typically carried out by contacting one of the compounds of Formula I with an equivalent amount of a mild oxidizing agent such as meta-chloroperbenzoic acid in a solvent such as methylene choride. The oxidation is typically carried out at a temperature range of from 0 to 25° C. for a period of time ranging from 1 to 24 hours. After the oxidation is completed, the desired compound of Formula I can be recoverd by extraction and purified by flash chromatography or recrystallization as is known in the art.

If X is to be represented by a sulfoxide substituent, then a strong oxidizing agent such as peracetic acid is utilized. The oxidation is typically carried out at a temperature range of from 25° C. to 50° C. for a period of time ranging from 1 to 6 hours in a solvent such as acetic acid. Alternatively, the oxidation can be carried out by utilizing a large molar excess of a mild reducing agent such as meta-chloroperbenzoic acid (MCPBA)

The oxidizing agent will typically be present in at least a 2 molar excess.

The compounds of Formula I are excitatory amino acid antagonists. They antagonize the effects which excitatory amino acids have upon the NMDA receptor complex. They preferentially bind to the strychnine-insensitive glycine binding site associated with the NMDA receptor complex. They are useful in the treatment of a number of disease states.

The compounds exhibit anti-convulsant properties and are useful in the treatment of epilepsy. They are useful in the treatment of grand mal seizures, petit mal seizures, psychomotor seizures, autonomic seizures, etc. One method of demonstrating their anti-epileptic properties is by their ability to inhibit the seizures that are caused by the administration of quinolinic acid. This test can be conducted in the following manner.

One group containing ten mice are administered 0.01–100 μg of test compound intracerebroventricularly in a volume of 5 microliters of saline. A second control group containing an equal number of mice are administered an equal volume of saline as a control. Approximately 5 minutes later, both groups are administered 7.7 micrograms of quinolinic acid intracerebroventricularly in a volume of 5 microliters of saline. The animals are observed for 15 minutes thereafter for signs of clonic-tonic seizures. The control group will have a statistically higher rate of clonic-tonic seizures than will the test group.

Another method of demonstrating the anti-epileptic properties of these compounds is by their ability to inhibit audiogenic convulsions in DBA/2 mice. This test can be conducted in the following manner. Typically one group of from 6–8 male DBA/2J audiogenic susceptible mice are administered from about 0.01 μg to about 100 μg of the test compound. The test compound is administered intracerebrally into the lateral ventricle of the brain. A second group of mice are administered an equal volume of saline control by the same route. Five minutes later the mice are placed individually in glass jars and are exposed to a sound stimulus of 110 decibels for 30 seconds. Each mouse is observed during the sound exposure for signs of seizure activity. The control group will have a statistically higher incidence of seizures than the group which receives the test compound.

The compounds of Formula I are useful for preventing or minimizing the damage which nervous tissues contained within the CNS suffer upon exposure to either ischemic, hypoxic, or hypoglycemic conditions or as the result of physical trauma. Representative examples of such conditions include strokes or cerebrovascular accidents, hyperinsulinemia, cardiac arrest, physical trauma, drownings, suffocation, and neonatal anoxic trauma. The compounds should be administered to the patient within 24 hours of the onset of the hypoxic, ischemic, or hypoglycemic condition in order for the compounds to effectively minimize the CNS damage which the patient will experience.

The compounds are also useful in the treatment of neurodegenerative diseases such as Huntington's disease, Alzheimer's disease, senile dementia, glutaric acidaemia type I, multi-infarct dementia, and neuronal damage associated with uncontrolled seizures. The administration of these compounds to a patient experiencing such a condition will serve to either prevent the patient from experiencing further neurodegeneration or it will decrease the rate at which the neurodegeneration occurs.

As is apparent to those skilled in the art, the compounds will not correct any CNS damage that has already occurred as the result of either disease, or a lack of oxygen or sugar. As used in this application, the term "treat" refers to the ability of the compounds to prevent further damage or delay the rate at which any further damage occurs.

The compounds exhibit an anxiolytic effect and are thus useful in the treatment of anxiety. These anxiolytic properties can be demonstrated by their ability to block distress vocalizations in rat pups. This test is based upon the phenomenon that when a rat pup is removed from its litter, it will emit an ultrasonic vocalization. It was discovered that anxiolytic agents block these vocalizations. The testing methods have been described by Gardner, C.R., Distress vocalization in rat pups: a simple screening method for anxiolytic drugs. *J. Pharmacol. Methods*, 14:181–187 (1985) and Insel et al. Rat pup ultrasonic isolation calls: Possible mediation by the benzodiazepine receptor complex. *Pharmacol. Biochem. Behav.*, 24: 1263–1267 (1986).

The compounds also exhibit an analgesic effect and are useful in controlling pain.

In order to exhibit these therapeutic properties, the compounds need to be administered in a quantity sufficient to inhibit the effect which the excitatory amino acids have upon the NMDA receptor complex. The dosage range at which these compounds exhibit this antagonistic effect can vary widely depending upon the particular disease being treated, the severity of the patient's disease, the patient, the particular compound being administered, the route of administration, and the presence of other underlying disease states within the patient, etc. Typically the compounds exhibit their therapeutic effect at a dosage range of from about 0.1 mg/kg/day to about 50 mg/kg/day for any of the diseases or conditions listed above. Repetitive daily administration may be desirable and will vary according to the conditions outlined above.

The compounds of the present invention may be administered by a variety of routes. They are effective if administered orally. The compounds may also be administered parenterally (i.e. subcutaneously, intravenously, intramuscularly, intraperitoneally, or intrathecally).

Pharmaceutical compositions can be manufactured utilizing techniques known in the art. Typically an antagonistic amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

As used in this application:
a) the term "patient" refers to warm blooded animals such as, for example, guinea pigs, mice, rats, cats, rabbits, dogs, monkeys, chimpanzees, and humans;
b) the term "treat" refers to the ability of the compounds to either relieve, alleviate, or slow the progression of the patient's disease;
c) the term "neurodegeneration" refers to a progressive death and disappearance of a population of nerve cells occurring in a manner characteristic of a particular disease state and leading to brain damage.

The compounds of Formula I may also be admixed with any inert carrier and utilized in laboratory assays in order to determine the concentration of the compounds within the serum, urine, etc., of the patient as is known in the art.

Neurodegenerative diseases are typically associated with a loss of NMDA receptors. Thus, the compounds of Formula I may be utilized in diagnostic procedures to aid physicians with the diagnosis of neurodegenerative diseases. The compounds may be labelled with imaging agents known in the art such as isotopic atoms and administered to a patient in order to determine whether the patient is exhibiting a decreased number of NMDA receptors and the rate at which that loss is occurring.

The following Examples are presented in order to further illustrate the present invention. However they should not be construed as limiting the claimed scope.

EXAMPLE I

The purpose of this example is to demonstrate one method for preparing one of the indole starting materials as described by structure (1) at Reaction Scheme I. Other methods known in the are are equally suitable.

3,5-Dichlorophenyhydrazone of ethyl pyruvate 3,5-Dichlorophenylhydrazine HCl (28.9 g; 135 mmol) was dissolved in 250 mL of ethanol (dry). Ethyl pyruvate (15.72 g; 14.8 mL; 135 mmol) was added and 2.5 mL of concentrated sulfuric acid was added. This was stirred at room temperature under argon for 1 hr., tlc ($CH_2Cl_2$) indicated no starting material.

The solvent was evaporated off under vacuum and the residue was taken up in ethyl acetate and washed with saturated sodium bicarbonate solution. The organic layer was dried over magnesium sulfate and concentrated to yield 41.7 g of a white solid; 3,5-Dichlorophenyhydrazone of ethyl pyruvate. This material was used without further purification. Both E and Z isomers are obtained.

$^1$H NMR ($CDCl_3$, 90 MHz) isomer A, $\delta$11.9 (b, 1H), 7.0 (d, 2H), 6.8 (d, 1H), 4.2 (q, 2H), 2.1 (s, 3H), 1.3 (t, 3H); isomer B $\delta$7.9 (b, 1H), 7.2-6.8 (m, 3H), 4.3 (q, 2H), 2.1 (s, 3H), 1.4 (t, 3H).

2-Carboxyethyl-4,6-dichloroindole 530 g of polyphosphoric acid was added to 41.7 g of 3,5-Dichlorophenyhydrazone of ethyl pyruvate. This was heated in a 95° C. oil bath overnight under argon with mechanical stirring. the reaction was allowed to cool to room temperature, and the reaction was poured onto ice. the resulting suspension was extracted with ethyl acetate, the organic layer was washed with saturated sodium bicarbonate solution, saturated sodium chloride solution, dried over magnesium sulfate, and concentrated to yield 88.2 g of a black solid.

The solid was suspended in ethanol (800 mL) and concentrated sulfuric acid (2 mL) was added and this was stirred overnight at room temperature under argon. The solvent was removed and the residue was taken up in ethyl acetate and washed with water, saturated sodium bicarbonate, and saturated sodium chloride solution. The organic layer was dried over magnesium sulfate and concentrated to yield 29.8 g of a brown solid.

This solid was recrystallized from ethyl acetate to yield 9.27 g of a yellow solid, a second crop gave 6.14 g of a yellow solid. The solids were combined and recrystallized from ethyl acetate/hexanes to yield 8.86 g of pale yellow needles; mp 183°-183.5° C.; 25% yield from 3,5-dichlorophenylhydrazine.HCl; IR (KBr) 3406, 3314, 1698, 1568, 1324, 1244, 1214, 840, 770 cm$^{-1}$; $^1$H NMR (DMSO-d$_6$, 300 MHz) $\delta$12.4 (b, 1H), 7.5 (s, 1H), 7.3 (s, 1H), 7.1 (s, 1H), 4.4 (q, 2H, J=7 Hz), 1.4 (t, 3H, J=7 Hz); $^{13}$C NMR (DMSO-d6, 75 MHz) $\delta$160.6, 137.6, 129.2, 129.1, 126.9, 124.3, 120.0, 111.4, 105.3, 61.0, 14.2; MS (CI/CH$_4$) m/z 258 (M+H)$^+$; Anal. Calcd for $C_{11}H_9Cl_2NO_2$: C, 51.19; H, 3.51; N, 5.43. Found: C, 51.38; H, 3.42; N, 5.53.

EXAMPLE II

The purpose of this example is to demonstrate one of the bromination reactions of Reaction Scheme I.

3-Bromo-2-carboxyethyl-4,6-dichloroindole

The starting indole ester 2-Carboxyethyl-4,6-dichloroindole (4.5 g; 17 mmol) was dissolved in pyridine (4.4 mL/mmol) and cooled in an ice/water bath under argon. Pyridium bromide perbromide (1.05 eq.) in pyridine (5.5 mL/mmol) was added dropwise, the solution turned red and a white precipitate appeared. After the addition was complete, ice water was added to the reaction. This was extracted with diethyl ether (2 times). The organic layer was dried over magnesium sulfate and concentrated to yield a white solid.

4.0 g crystallized analytically pure upon concentration. The mother liquor gave an additional 1.91 g of 3-Bromo-2-carboxyethyl-4,6-dichloroindole as a white solid. 5.91 g; 100% yield; mp 228°-228.5° C. IR (KBr) 3302, 1676, 1612, 1556, 1510, 1424, 1250, 838, 776 cm$^{-1}$; $^1$H NMR (DMSO-d$_6$, 300 Hz) $\delta$12.7 (b, 1H), 7.5 (s, 1H), 7.3 (s, 1H), 4.4 (q, 2H, J=7.1 Hz), 1.4 (t, 3H, J=b 7.1 Hz); $^{13}$H NMR (DMSO-d$_6$, 75 MHz) $\delta$159.6, 137.0, 129.7, 127.1, 126.2, 122.2, 120.7, 111.9, 93.8, 61.2, 14.2; MS (CI/CH$_4$) m/z 336 (M+H)$^+$; Anal. Calcd for $C_{11}H_8BrCl_2NO_2$: C, 39.20; H, 2.39; N, 4.16. Found: C, 39.20; H, 2.38; N, 4.36.

EXAMPLE III

The purpose of this example is to demonstrate one of the displacement reactions of Reaction Scheme I.

3-[(Carbethoxymethyl)thio]-2-carbethoxy-4,6-dichloroindole

The starting bromo indole ester 3-bromo-2-carbxyethyl-4,6-dichloroindole (3.0 g; 8.9 mmol), ethyl-2-mercaptoacetate (1.75 eq.) and potassium carbonate (1.75 eq.) were combined in acetone (20 mL/mmol) and refluxed under argon, until tlc indicates no starting material present. The reaction was allowed to cool to room temperature and the solvent was evaporated off under vacuum. The resulting residue was taken up in diethyl ether and washed with water. The aqueous layer was extracted with diethyl ether. The combined organic layers were dried over magnesium sulfate and concentrated to give a white solid.

The white solid was placed on a silica gel flash column eluting with 20% EtOAc/hexane. The purified product was recrystallized from hexane/ethyl acetate to yield 3-[(Carbethoxymethyl)thio]-2-carbethoxy-4,6-dichloroindole as analytically pure crystals. 1.1 g; 33% yield (67% based on recovered starting material); mp 152.5°–153° C.; IR (KBr) 3262, 2982, 1718, 1704, 1504, 1408, 1302, 1284, 1270, 1214, 1194, 1172, 1130, 1052, 1028, 834 cm$^{-1}$; $^1$H NMR (CDCl$_3$, 300 MHz) δ10.1 (b, 1H), 7.1 (s, 1H), 6.8 (s, 1H), 4.4 (q, 2H, J=7.1 Hz), 4.2 (q, 2H, J=7.1 Hz), 3.6 (s, 2H), 1.5 (t, 3H, J=7.1 Hz), 1.3 (t, 3H, J−=7.1 Hz); $^{13}$C NMR (CDCl$_3$, 75 MHz) δ171.2, 160.1, 136.5, 130.8, 130.7, 128.2, 124.4, 123.5, 110.8, 110.3, 61.7, 61.6, 39.1, 14.2, 14.0; MS (CI/CH$_4$) m/z 176 (M+H)$^+$; Anal Calcd for C$_{15}$H$_{15}$Cl$_2$NO$_4$S: C, 47.88; H, 4.02; N, 3.72. Found: C, 47.81; H, 4.03; N, 3.62.

EXAMPLE IV

This example demonstrates one of the deprotection reactions at Reaction Scheme I.

3-[(Carboxymethyl)thio]-2-carboxy-4,6-dichloroindole

The starting diester 3-[(Carbethoxymethyl)thio]-2-carbethoxy-4,6-dichloroindole (1.0 g; 2.7 mmol) was suspended in a 1:1 mixture of water: tetrahydrofuran (5 mL/mmol). Lithium hydroxide (3 eq.) was added and this reaction was stirred overnight at room temperature under argon. The reaction was diluted with ethyl acetate and water. The layers were separated and the aqueous layer was acidified with concentrated hydrochloric acid. This was extracted with ethyl acetate and the organic layer was dried over magnesium sulfate and concentrated to yield a white solid. This white solid was recrystallized from ethyl acetate/hexane to give 3-[(Carboxymethyl)thio]-2-carboxy-4,6-dichloroindole. 0.51 g; 60% yield; mp 152.5–153° C.; IR (KBr) 3258, 3160, 1740, 1724, 1614, 1506, 1402, 1368 1338, 1272, 1240, 1180, 840 cm$^{-1}$; $^1$H NMR (DMSO-d$_6$, 300 MHz) δ3.0 (b, 2H), 12.6 (s, 1H), 7.5 (s, 1H), 7.3 (s, 1H), 3.6 (s, 2H); $^{13}$C NMR (DMSO-d$_6$, 75 MHz) δ170.5, 161.3, 137.0, 132.7, 128.9, 127.6, 124.1, 122.1, 111.7, 108.9, 39.4; MS (CI/CH$_4$) m/z 320 (M+H)$^+$, 302, 274, 262, 244; Anal. Calcd for C$_{11}$H$_7$Cl$_2$NO$_4$S: C, 41.27; H, 2.20; N, 4.38. Found: C, 40.93; H, 1.88; N, 4.16.

EXAMPLE V

This example demonstrates the preparation of

3-Bromo-2-carbethoxyindole

The above compound was prepared from 2-carbethoxyindole (1.16 g, 11.4 mmol) using the procedure described at Example II. Recrystallization from ethyl acetate/hexane afforded 3-Bromo-2-carbethoxyindole as colorless needles (2.6 g, 80%): mp 150°–152° C.; NMR (CDCl$_3$) δ9.15 (broad multiplet, 1H), 7.67 (m, 1H), 7.38 (m, 2H), 7.22 (m, 1H), 4.48 (q, J=7.0 Hz, 2H), 1.46 (t, J=7.0 Hz, 3H). Anal. calcd for C$_{11}$H$_{10}$BrNO$_2$: C, 49.28; H, 3.76; N, 5.22. Found: C, 49.39; H, 3.79; N, 5.08.

EXAMPLE VI

3-[(Carbethoxymethyl)thio]-2-carbethoxyindole

The above material was prepared from 3-Bromo-2-carbethoxyindole using the procedure described in Example III. 0.5 g; 17% yield; IR (KBr) 3274, 2980, 1705, 1516, 1412, 1374, 1366, 1324, 1306, 1290, 1252, 1232, 1222, 1132, 1058, 1032, 744 cm$^{-1}$; $^1$H NMR (CDCl$_3$, 300 MHz) δ9.2 (b, 1H), 7.9 (d, 1H, J=8 Hz), 7.4–7.2 (m, 3H), 4.5 (q, 2H, J=7.1 Hz), 4.0 (q, 2H, J=7.2 Hz); 3.6 (s, 2H), 1.5 (t, 3H, J=7.1 Hz), 1.1 (t, 3H, J=7.2 Hz); $^{13}$C NMR (CDCl$_3$, 75 MHz) δ170.0, 160.8, 135.1, 130.6, 128.7, 126.1, 121.4, 121.3, 111.9, 111.7, 61.4, 61.2, 38.0, 14.3, 13.8; MS (CI/CH$_4$) m/z 308 (M+H)$^+$; Anal. Calcd for C$_{15}$H$_{17}$NO$_4$S: C, 58.61; H, 5.58; N, 4.56. Found: C, 58.25; H, 5.55; N, 4.31.

EXAMPLE VII

This example demonstrates the preparation of

3-[(Carboxymethyl)thio]-2-carboxyindole

The above material was prepared from 3-[(Carbethoxymethyl) thio]-2-carbethoxyindole (0.42 g, 1.39 mmol) using the procedure described in Example IV. 0.25 g of 3-[(Carboxymethyl)thio]-2-carboxyindole; 72% yield; mp 194°–195° C. (dec.); IR (KBr) 3408, 3054, 3008, 1706, 1636, 1512, 1440, 1420, 1396, 1322, 1278, 1232, 1138, 740 cm$^{-1}$; $^1$H NMR (DMSO-d$_6$, 300 MHz) δ12.9 (b, 2H), 12.1 (s, 1H), 7.7 (d, 1H, J=8 Hz), 7.5 (d, 1H, J=8.3 Hz), 7.3 (m, 1H), 7.2 (m, 1H), 3.6 (s, 2H); $^{13}$C NMR (DMSO-d$_6$, 75 MHz) δ170.9, 161.9, 135.5, 129.8, 129.3, 124.9, 120.6, 120.5, 112.8, 109.4, 37.6; MS (CI/CH$_4$) m/z 252 (M+H)$^+$, 234, 206, 194; MS (EI) m/z 251 (M+), 188, 174, 161, 146; Anal. Calcd for C$_{11}$H$_9$NO$_4$S: C, 52.58; H, 3.61; N, 5.58. Found: C, 52.50; H, 3.54; N, 5.49.

EXAMPLE VIII

This example demonstrates one of the oxidation reactions of Reaction Scheme II.

3-[(Carbethoxymethyl)sulfinyl]-2-carbethoxyindole

3-[(Carbethoxymethyl)thio]-2-carbethoxyindole is treated with m-chloroperbenzoic acid (1 eq.) in methylene chloride at 0° C. The reaction is followed by TLC. After starting material is consumed the reaction mixture is washed with sat. NaHCO$_3$ and sat. NaCl. The organic layer is dried. 3-[(Carbethoxymethyl)sulfinyl]-2-carbethoxyindole may be isolated by flash column chromatography followed by recrystallization.

EXAMPLE IX

This example demonstrates one of the oxidation reactions to produce a sulfoxide derivative.

3-[(Carbethoxymethyl)sulfonyl]-2-carbethoxy-4,6-dichloroindole

3-[(Carbethoxymethyl)thio]-2-carbethoxy-4,6-dichloroindole is reacted with an excess of peracetic acid in acetic acid at 50° C. After consumption of starting material the reaction is worked up as in Example VIII which produces 3-[(Carbethoxymethyl)sulfonyl]-2-carbethoxy-4,6-dichloroindole.

EXAMPLE X

3-[(2-(2-dimethylamino)ethoxycarbonylmethyl)thio]-2-(2-dimethylamino)ethoxycarbonyl-4,6-dichloroindole 3-[(Carbethoxymethyl)thio]-2-carbethoxy-4,6-dichloroindole is dissolved in toluene, to which an excess of dimethylaminoethanol is added followed by an excess amount of $K_2CO_3$. The reaction is heated to reflux. After consumption of starting material the reaction is diluted with EtOAc, washed with water and dried ($MgSO_4$). The organic layer is removed in vacuo and the residue is purified by flash chromatography and subsequent recrystallization which will yield 3-[(2-(2-dimethylamino)ethoxycarbonylmethyl)thio]-2-(2-dimethylamino) ethoxycarbonyl-4,6-dichloroindole.

EXAMPLE XII

3-[(Carboxamidomethyl)thio]-2-carboxamidoindole

3-[(Carboxymethyl)thio]-2-carboxyindole is dissolved in THF. To this solution is added triethylamine (2 eq.) and DCC (2 eq.). Ammonia gas is then bubbled through the system for several minutes. The reaction is worked up by diluting in ethylacetate, washing with 1NHCl, sat. $NaHCO_2$ and sat. NaCl. The organic layer is dried ($MgSO_4$) and concentrated in vacuo. The product, 3-[(carboxamidomethyl)thio]-2-carboxamidoindole, may be purified by flash chromatography and/or recrystallization.

What is claimed is:

1. A compound of the formula :

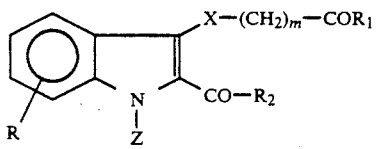

Formula I in which Z is represented by H, $C_{1-4}$ alkyl, phenyl, substituted phenyl, or an alkylphenyl substituent in which the phenyl ring may be optionally substituted; X is represented by S, SO, or $SO_2$; m is represented by an integer from 1–4; R is represented by hydrogen, halogen, $C_{1-4}$ alkyl, $C_{1-4}$ alkoxy, $CF_3$, $OCF_3$, OH, $NO_2$, or CN; $R_1$ and $R_2$ are each independently represented by —OH, —$OR_3$, —$NR_4R_5$, —$OCH_2OR_3$, or —O—$(CH_2)_n$-$NR_6R_7$, in which n is an integer from 1–4; $R_3$ is represented by $C_{1-4}$ alkyl, phenyl, substituted phenyl or an alkylphenyl substituent in which the phenyl ring may be optionally substituted; $R_4$ and $R_5$ are each independently represented by hydrogen or a $C_{1-4}$ alkyl; $R_6$ and $R_7$ are each independently represented by hydrogen Or a $C_{1-4}$ alkyl or $R_6$ and $R_7$ together with the adjacent nitrogen atom form a piperidino, morpholino or pyrrolidino group; and the pharmaceutically acceptable addition salts thereof.

2. A compound according to claim 1 wherein R represents a 4,6-dichloro substituent.

3. A compound according to claim 1 wherein X is S.

4. A compound according to claim 1 wherein X is SO.

5. A compound according to claims 1 wherein X is $SO_2$.

6. A method for antagonizing the effects of excitatory amino acids upon the NMDA receptor complex comprising administering to a patient in need thereof, an antagonistic amount of a compound according to claim 1.

7. A method for the treatment of epilepsy comprising administering to a patient in need thereof an anti-epileptic amount of a compound according to claim 1.

8. A method for the treatment of neurodegenerative diseases comprising administering to a patient in need thereof an effective amount of a compound according to claim 1.

9. A method for preventing ischemic/hypoxic/hypoglycemic damage to cerebral tissue comprising administering to a patient in need thereof an effective amount of a compound according to claim 1.

10. A method for the treatment of anxiety comprising administering an anxiolytic amount of a compound according to claim 1.

11. A method for producing an analgesic effect comprising administering to a patient in need thereof an analgesic amount of a compound according to claim 1.

12. A pharmaceutical composition comprising a compound according to claim 1 in admixture with a pharmaceutically acceptable carrier.

13. A compound according to claim 2 in which m is 1.

14. A compound according to claim 13 in which Z is H.

15. A compound according to claim 1 in which said compound is 3-[(carboxymethyl)thio]-2-carboxy-4,6-dichloroindole.

16. A compound according to claim 1 in which said compound is 3-[(carbethoxymethyl)thio]-2-carbethoxyindole.

17. A compound according to claim 1 in which said compound is 3-[(carbethoxymethyl)thio]-2-carbethoxyindole.

18. A compound according to claim 1 in which said compound is 3-[(carboxymethyl)sulfinyl]-2-carboxyindole.

19. A compound according to claim 1 in which said compound 3-[(carboxymethyl)sulfonyl]-2-carboxyindole.

20. A compound according to claim 1 in which said compound is 3-[(2-(2-dimethylamino)ethoxycarbonylmethyl)thio]-2-(2-dimethylamino)ethoxycarbonyl-4,6-dichloroindole.

21. A compound according to claim 1 in which said compound is 3-[(carboxamidomethyl)thio]-2-carboxamidoindole.

22. A compound according to claim 1 in which said compound is 3-[(carboxymethyl)thio]-2-carboxy-6-fluoroindole.

23. A compound according to claim 1 in which said compound is 3-[(carboxymethyl)thio]-2-carboxy-4,6-difuloroindole.

24. A compound according to claim 1 in which said compound is 3-[(carbethoxymethyl)sulfinyl]-2-carbethoxyindole.

25. A compound according to claim 1 in which said compound is 3-[(carbethoxymethyl)sulfonyl]-2-carbethoxy-4,6-dichloroindole.

* * * * *